United States Patent [19]

Fujii et al.

[11] Patent Number: 5,238,917

[45] Date of Patent: Aug. 24, 1993

[54] HIGH-ABSORBABLE TRANSVAGINAL PREPARATION CONTAINING BIOLOGICALLY ACTIVE POLYPEPTIDE

[75] Inventors: Takeru Fujii, Naruto; Seiichi Sakoh, Anan; Toru Hibi, Kawasaki; Shigeyuki Takama, Tokushima; Akiya Yamada, Takamatsu, all of Japan

[73] Assignees: Teikoku Seiyaku Kabushiki Kaisha, Kanagawa; Asahi Kasei Kogyo Kabushiki Kaisha, Osaka, Japan

[21] Appl. No.: 577,108

[22] Filed: Sep. 4, 1990

[30] Foreign Application Priority Data

Sep. 11, 1989 [JP] Japan .................. 1-235186

[51] Int. Cl.$^5$ .............. A61K 37/00; A61K 37/02; C07K 5/00
[52] U.S. Cl. ........................... 514/2; 514/12; 514/967; 530/307; 424/430
[58] Field of Search .............. 514/3, 12, 2, 967; 424/433, 430; 530/307

[56] References Cited

U.S. PATENT DOCUMENTS

| | | |
|---|---|---|
| 3,888,838 | 6/1975 | Immer et al. . |
| 3,917,825 | 11/1975 | Matsuzawa et al. . |
| 4,010,125 | 3/1977 | Schally et al. . |
| 4,018,726 | 4/1977 | Schally et al. . |
| 4,083,967 | 4/1978 | Beddell et al. . |
| 4,234,571 | 11/1980 | Nestor et al. . |
| 4,609,640 | 9/1986 | Morishita et al. .......... 514/12 |
| 4,659,696 | 4/1987 | Hirai et al. . |
| 4,670,419 | 6/1987 | Uda et al. . |
| 4,873,087 | 10/1989 | Morishita et al. .......... 424/433 |
| 4,994,273 | 2/1991 | Zentner et al. ............ 424/427 |

FOREIGN PATENT DOCUMENTS

| | | |
|---|---|---|
| 0115627 | 12/1983 | European Pat. Off. . |
| 0183527 | 11/1985 | European Pat. Off. . |
| 0193372 | 2/1986 | European Pat. Off. . |
| 0332222 | 3/1989 | European Pat. Off. . |
| 56-122309 | 9/1981 | Japan . |
| 127689A | 10/1983 | United Kingdom . |

OTHER PUBLICATIONS

Azaz et al. CA 96:74626N (1982), Israeli el 54,041 May 20, 1981 appl Feb. 13, 1978.
Chemical Abstract, vol. 109, No. 14, Oct. 3, 1988, p. 632, abstracts no. 115972e, Columbus, Ohio; Y. Nakada et al.
European Search Report.
Saito et al., Fertility and Sterility, vol. 28, No. 3, 1977, pp. 240-245.
Topics in Pharmaceutical Sciences, 1987, pp. 445-455, Muranishi et al.
Okada et al., J. Pharm. Sci., vol. 72, No. 1, Jan. 1983, 75-78.
Touitou et al., J. Pharm. Pharmac., 1978, 30, 662-663.
Morimoto et al., J. Pharm. Pharmacol. 1985, 37, 759-760.

*Primary Examiner*—Merrell C. Cashion, Jr.
*Assistant Examiner*—B. Celsa
*Attorney, Agent, or Firm*—Birch, Stewart, Kolasch & Birch

[57] ABSTRACT

A high-absorbable transvaginal preparation having excellent absorbability of the active ingredient, which comprises a biologically active polypeptide and an absorption promoter comprising a polyoxyethylenealkylphenyl ether and one or more compounds selected from the group consisting of an N-acylamino acid, cholic acids, pectic acid, taurine, saccharin, glycyrrhizic acid, aspartame, or a salt thereof.

11 Claims, No Drawings

HIGH-ABSORBABLE TRANSVAGINAL PREPARATION CONTAINING BIOLOGICALLY ACTIVE POLYPEPTIDE

The present invention relates to a high-absorbable transvaginal preparation containing a biologically active polypeptide, more particularly to a high-absorbable preparation for transvaginal administration which comprises a biologically active polypeptide and a mixture of polyoxyethylenealkylphenyl ether and a specific compound as an absorption promoter for the purpose of enhancing the absorbability of said polypeptide.

TECHNICAL BACKGROUND AND PRIOR ART

Polypeptide hormones such as insulin, calcitonin, and the like are a water-soluble high molecular weight compound which is easily decomposed by gastric juice or a protease such as pepsin, trypsin, and the like. Accordingly, when these polypeptide are orally administered, they are almost decomposed without being absorbed and hence, they hardly show the effective physiological activity thereof. Therefore, at present, the pharmaceutical composition of these polypeptides are usually prepared in a suitable form for injection in order to obtain the desired biological activity thereof. However, when the polypeptides need to be administered at regular intervals and repeatedly, the injection route is inconvenient and painful for patients, and hence, recent attention has been given to efforts for developing other administration methods for polypeptides instead of by the injection route.

A pharmaceutical composition for administration into the nasal cavity, the vagina or the rectum has been disclosed in Hirai et al., U.S. Pat. No. 4,659,696 and Uda et al., U.S. Pat. No. 4,670,419, which comprises a hydrophilic drug which is hardly absorbed in the gastrointestinal tract and cyclodextrin. The hydrophilic drug used in the said pharmaceutical composition includes polypeptides such as insulin, LH-RH analogue, oxytocin, TRH, and the like. The cyclodextrin used in this pharmaceutical preparation is preferably α-cyclodextrin. Various additives are also contained in said composition.

Further, a pharmaceutical composition for administration into the rectum or the vagina is disclosed in Morishita et al., U.S. Pat. No. 4,609,640, which comprises a water-soluble drug and a specific type water-soluble chelating agent and will show excellent absorbability of the drug. The water-soluble drug used in the said pharmaceutical composition includes polypeptides such as insulin, somatostatin, calcitonin, and the like. When a chelating agent with low molecular weight such as a polycarboxylic acid is used together, a water-soluble high molecular weight base which does not have chelating activity, for example, gelatin, casein, albumin, globulin is also used. Other conventional additives which are necessary for these administration dosage forms, for example, a surfactant, may also be contained therein.

Moreover, a transnasal powder preparation is disclosed in European Patent Publication EP-A-0193372, which comprises a physiologically active polypeptide, a quaternary ammonium compound and a lower alkyl ether of cellulose, which will have excellent preservability and chemical stability. The preferred powder preparation comprises insulin or calcitonin, benzalkonium chloride and hydroxypropyl cellulose. Various conventional additives, for example, lubricants, waxes, binding agents, diluents, colorants, flavoring agents, antioxidants, fillers, isotonic agents, surfactants, and the like are also contained therein.

Further, an absorbable intranasal preparation of calcitonin is disclosed in European Patent Publication EP-A-0183527, which comprises a calcitonin and at least one absorption promoter selected from the group consisting of acids or a salt thereof, benzilic acid or a salt thereof, capric acid or a salt thereof, polyethylene glycol 400, pyridoxal or a salt thereof, malic acid or a salt thereof and pyrophosphoric acid or a salt thereof. Other conventional additives for intranasal preparations may be added thereto. It is thought that by using one of these specific absorption promoters, the efficiency of absorbing through the nasal cavity membrane is improved. The above mentioned patent application says that a surfactant had been used as an absorption promoter in order to improve the absorbability through the nasal cavity of a large polypeptide such as calcitonin in the beginning. Both amphoteric and cationic surfactants, especially nonionic surfactant, polyoxyethylenelauryl ether had been used in the early studies. However, it is assumed that such a desirable ether-type surfactant enhances the absorbability of a medicament by destroying the nasal cavity membrane.

British Patent Application No. 8326436 which is published under GB-2127689A discloses an intranasal preparation, which comprises calcitonin incorporated into a suitable liquid diluent or carrier for administration into nasal cavity mucous membrane, benzalkonium chloride and/or a surfactant being suitable for administration into the nasal cavity. When the said preparation contains a surfactant, the surfactant is preferably a nonionic surfactant, more preferably polyoxyalkylene higher alcohol ether. It is reported that by these transnasal preparations of calcitonin, the bioavailability of calcitonin and the stability thereof are improved.

Moreover, a pharmaceutical composition of LH-RH or an analogue thereof for administration into the rectum or the vagina is disclosed in Matsuzawa et al. U.S. Pat. No. 3,917,825. In the said composition, it is preferable that nonapeptide or decapeptide is uniformly dispersed into an oil base (e.q. oil, wax or fatty acid triglyceride) containing a nonionic surfactant such as polyoxyethylene higher alcohol ether, and the like. Various administration methods including the transvaginal route of the nonapeptide or decapeptide are disclosed in numerous patent applications and patent publications such as Beddell et al., U.S. Pat. No. 4,083,967, Immer et al., U.S. Pat. No. 3,888,838, Nestor et al., U.S. Pat. No. 4,234,571, Schally et al., U.S. Pat. Nos. 4,010,125 and 4,018,726, and Saito et al., Fertility and Sterility, Vol. 28, No. 3, March 1977, 240–245.

Further, there is disclosed potent transvaginal adsorption of LH-RH analogue (leuprolide), LH-RH itself, and insulin in Okada et al., J. Pharm. Sci., Vol. 72, No. 1, January 1983, 75–78. The increase in absorbability thereof is obtained by using an organic acid. The enhancing effect on the absorbability seems to correlate with the chelation property of the organic acid to be used [cf. Okada et al., J. Takeda Res. Lab. 42 ($\frac{1}{2}$), 150 (1983)].

Touitou et al. developed a hydrophilic preparation for administration into the rectum or the vagina of insulin, heparin, phenol red and gentamicin which comprises as an nonionic surfactant polyethylene glycol together with cetomacrogol 1000 (polyethylene glycol 1000 monocetyl ether) (cf. J. Pharm. Pharmac., 1978, 30, 663). IL 54041 of the Jerusalem University seems to relate to the similar study to the above, which discloses an enteric coated preparation and a transvaginal preparation of peptide hormone or heparin containing a nonionic surfactant.

Morimoto et al. reported in J. Pharm. Pharmacol. 1985, 37, 759–760 the effect of nonionic surfactants, polyoxyethylene sorbitan monooleate and polyoxyethylene(9)lauryl ether, and the absorption promoting property of polyacrylic acid gel base on the adsorption at the rectum of semi-synthesized analogue of eel calcitonin. It was discovered at the early stage that polyacrylic acid gel base improves the absorption of insulin administered into the rectum, the vagina and the nasal cavity, and also the adsorption of calcitonin administered into the rectum or the nasal cavity. The early report indicates that the absorbability of hardly absorbable drug is improved by administering thereof together with enamine, carboxylic acid and a surfactant.

There is disclosed an intrarectal preparation of calcitonin in Japanese Patent Publication No. 56-122309, wherein calcitonin and a surfactant (e.g. cholic acid, saponin, phospholipid, polyoxyethylenealkyl ether, glycerin fatty acid ester, sorbitan fatty acid ester, etc.) are dispersed uniformly in a suppository base.

Moreover, there is disclosed absorption in the intestine of a drug by various compositions which promote absorption of a drug to be absorbed through the cell lining on the surface of the mucous membrane in Muranishi, S., "Absorption Barriers and Absorption Promoters in the Intestine" of Topics in Pharmaceutical Sciences, 1987. A mixed micelle is also disclosed therein, wherein a nonionic surfactant and an unsaturated aliphatic carboxylic acid are used.

Although there are many studies on the administration methods of polypeptides as mentioned above, these methods generally still have numerous defects. That is, when a drug is administered by one of above mentioned methods, it is necessary to administer the drug at a-higher dose thereof than when it is administered by the injection route. As a result, the absorbed amount of the drug fluctuates widely. Thus, it is desirable that dosage forms for a polypeptide are excellent in the storage stability, and the polypeptide therein is easily absorbed without stimulating the mucous membrane of the administered region, and stable at the administered region. Hitherto, although there have been many attempts to discover an alternative administration method of a biologically active polypeptide such as insulin, calcitonin and the like instead of by the conventional injection route, no attention has been given to the problem that the biologically active polypeptide tends to lose biological activity during storage. The requisite to obtain a stable pharmaceutical dosage form containing a biologically active polypeptide is important for preparing the above pharmaceutical compositions. Moreover, in the study on the alternatives to the injection route, the above mentioned prior arts do not suggest the way to avoid the enzymolysis of polypeptide which occurs during the process of absorption at the administered region.

BRIEF DESCRIPTION OF THE INVENTION

Taking into consideration the above mentioned problems, that is, in order to reduce the pain of patients by injection and to suppress the decomposition of polypeptide as much as possible, the present inventors have intensively studied an improved dosage form of biologically active polypeptide such as insulin, calcitonin, and the like, instead of an injection preparation, and have found that a transvaginal preparation containing only polyoxyethylenealkylphenyl ether hardly shows improvement of absorbability, and that although transvaginal preparations containing N-acylamino acid, cholic acids, pectic acid, taurine, saccharin, glycyrrhizic acid, or aspartame alone show improvement of absorbability, the absorption rate thereof is not sufficient, and hence, they have many problems associated therewith such as the necessity to increase the dose of biologically active polypeptide. As a result of further studies, the present inventors have unexpectedly found that the desired transvaginal preparation of a biologically active polypeptide having extremely excellent absorbability can be obtained by incorporating polyoxyethylenealkylphenyl ether together with one or more compounds selected from the group consisting of N-acylamino acids, cholic acids, pectic acid, taurine, saccharin, glycyrrhizic acid, aspartame or a salt thereof. That is, the present invention relates to a highly absorbable transvaginal preparation which comprises a biologically active polypeptide and, as an absorption promoter, polyoxyethylenealkylphenyl ether and one or more compounds selected from the group consisting of N-acylamino acids, cholic acids, pectic acid, taurine, saccharin, glycyrrhizic acid, aspartame or a salt thereof.

The object of the present invention is to provide a pharmaceutical dosage form of a biologically active polypeptide which is excellent in storage stability, and shows easy absorption of the polypeptide without irritating the mucous membrane of the administered region, and which is stable at the administered region.

DETAILED DESCRIPTION OF THE INVENTION

The biologically active polypeptide used in the present invention is a polypeptide having a comparatively lower molecular weight. Preferable biological active polypeptides of the present invention are, for example, insulin, angiotensin, vasopressin, desmopressin, LH-RH (luteinizing hormone-releasing hormone), somatostatin, calcitonin, glucagon, oxytocin, gastoline, somatomedin, secretin, h-ANP (human atrial natriuretic polypeptide), ACTH (adrenocorticotropic hormone), MSH (melanocyte stimulating hormone), β-endorphin, muramyldipeptide, enkephalin, neurotensin, bombesin, VIP (vasoactive intestinal polypeptide), CCK-8 (cholecystokinin-8), PTH (parathyroid hormone), CGRP (calcitonin gene relating polypeptide), TRH (thyrotropin-releasing hormone), endothelin, or a derivative (including an analogue) thereof. The various polypeptides which can be used in the present invention also include either naturally occurring polypeptides or synthesized derivatives (including analogue) thereof. Thus, for example, calcitonin which is used in the present invention and has a reducing activity on serum calcium level includes not only natural calcitonins such as salmon calcitonin, human calcitonin, porcine calcitonin, eel calcitonin or chicken calcitonin but also analogues such as [Asu1,7]-eel calcitonin (e.g. elcatonin), and the like. The most preferred polypeptides of the present invention are calcitonin, insulin and LH-RH.

The amount of a biologically active polypeptide contained in the transvaginal preparations of the present invention depends on the kind of the polypeptide, but it should be an effective amount for exhibiting the desired pharmaceutical activity thereof. For example, when calcitonin is employed as a biologically active polypeptide of the present invention, it should be contained therein in an effective amount thereof for treating a morbid condition such as Paget's disease, hypercalcemia or osteoporosis, and the like. For example, when porcine calcitonin is used, the amount thereof contained in the typical preparation may be in the range of about 0.01–about 0.8 I.U./mg, and when elcatonin is used, the amount thereof may be in the range of about 0.01–about 0.2 I.U./mg. When insulin is used as a biologically active polypeptide of the present invention, the effective amount for regulating the glucose level in blood and treating diabates is usually employed. Further, when LH-RH or an analogue thereof is used as a biologically active polypeptide of the present invention, the effective amount for treating various diseases of female genital organs, the effective amount for contraception and the effective amount for inducing other known biological responses to LH-RH are employed. When PTH, CGRH, somatomedin or an analogue thereof is used, the effective amount thereof for treating bone metabolic disorder is employed. The amount of other biologically active polypeptide which can be used in the present invention is also determined in the same way as above.

The absorption promoter of the present invention comprises a mixture of polyoxyethylenealkylphenyl ether and one or more compounds selected from the group consisting of N-acylamino acids, cholic acids, pectic acid, taurine, saccharin, glycyrrhizic acid, aspartame (N-L-α-aspartyl-L-phenylalanine 1-methyl ester) or a salt thereof.

Preferred polyoxyethylenealkylphenyl ether is polyoxyethylene(5-30)alkylphenyl ether, for example, polyoxyethylene(9)octylphenyl ether, polyoxyethylene(10)octylphenyl ether, polyoxyethylene(30)octylphenyl ether, polyoxyethylene(10)nonylphenyl ether, polyoxyethylene(15)nonylphenyl ether or polyoxyethylene(20)nonylphenyl ether. The most preferred polyoxyethylenealkylphenyl ether is polyoxyethylene(9-)octylphenyl ether [Nonidet P-40 (trade mark), hereinafter referred to as NP-40].

Preferred N-acylamino acid is amino acids N-acylated with an aliphatic carboxylic acid having 6–14 carbon atoms, especially having 8, 10 or 12 carbon atoms. A more preferred N-acylamino acid or a salt thereof is, for example, N-n-hexanoylglycine, N-n-octanoylglycine, N-n-decanoylglycine, N-n-dodecanoylglycine, N-n-decanoylglutamic acid, N-n-decanoylphenylalanine, N-n-decanoylaspartic acid, or an alkali metal salt thereof such as sodium salt, and the like.

The cholic acid includes, for example, deoxycholic acid, chenodeoxycholic acid, taurocholic acid, or an alkali metal salt thereof such as sodium salt, and the like.

Further, saccharin, taurine, glycyrrhizic acid and pectic acid may also be used in the form of a suitable alkali metal salt thereof such as sodium salt, and the like.

The amount of the absorption promoter contained in the transvaginal preparation of the present invention depends on the kind thereof, but usually, to the total weight of the transvaginal preparation, polyoxyethylenealkylphenyl ether is used in the range of about 0.1 to about 20% by weight, preferably about 0.5 to about 5% by weight, and one or more compounds selected from the group consisting of N-acylamino acids, cholic acids, pectic acid, taurine, saccharin, glycyrrhizic acid, aspartame or a salt thereof are used in the range of about 0.01 to about 5% by weight, preferably about 0.05 to about 2% by weight.

The transvaginal preparation of the present invention may contain, if necessary, animal protein and/or vegetable protein in order to enhance the stability of the biologically active polypeptide. The animal protein and/or vegetable protein are preferably selected from ones which have usually been used for foods or pharmaceutical compositions. Preferred animal protein is, for example, albumin (e.g. bovine serum albumin, human serum albumin, etc.), casein and gelatin, and the like. Among these, the most preferable animal protein is albumin. The vegetable protein which can be used in the present invention is, for example, gluten, zein, soybean protein, and the like. The animal protein and the vegetable protein may be used either alone or together in the appropriate ratio.

In the present invention, the animal protein and the vegetable protein are used only when it is necessary, such as when the biologically active polypeptide or a derivative thereof is unstable. The stability of various polypeptide is well known by those skilled in this field. For example, elcatonin is a modified eel calcitonin which is prepared by modifying eel calcitonin so as to increase the stability thereof, and hence, the above animal or vegetable protein is not essential for a pharmaceutical composition containing elcatonin. On the other hand, natural eel calcitonin is not so stable as elcatonin, and hence, it is necessary to use the animal protein and/or the vegetable protein in a pharmaceutical composition thereof in order to maintain the stability of the polypeptide. Most polypeptides and derivative thereof are unstable. There are available the informations as to the stability of the specific polypeptide from ordinary text books or specifications supplied by manufacturers.

The amount of the animal protein and/or the vegetable protein used in the transvaginal preparation of the present invention is an effective amount for maintaining the stability of the polypeptide, and depends on the kind of the polypeptides, but is usually in the range of about 0.001 to 25% (w/v).

The transvaginal preparation of the present invention is prepared in the conventional pharmaceutical dosage forms, for example, liquids, gels (preferably gel with high viscosity), suppositories, films, tablets, soft capsules, tampons, creams, and the like, which comprise usually a biologically active polypeptide, an absorption promoter and, if necessary, animal protein and/or vegetable protein.

The transvaginal preparation of the present invention can be prepared a conventional method. For instance, a liquid preparation can be prepared by dissolving a biologically active polypeptide, an absorption promoter and if necessary, animal protein and/or vegetable protein in a pharmaceutically acceptable liquid carrier or diluent such as purified water, a physiological saline solution or a buffer, optionally followed by subjecting the resulting solution to various forming processes. The gel preparation having a high viscosity can be prepared adding a conventional thickening agent into the above liquid preparation. The thickening agent is, for example, cellulose lower alcohol ether, PVA (polyvinyl alcohol), PVP (polyvinylpyrrolidone), polyoxyethyleneoxypropylene glycol block copolymer [Pluronic (trade mark)], and the like. Since the pH value of the transvaginal preparation of the present invention has preferably a pH value closest to that of the vagina, after dissolving a biologically active polypeptide, an absorption promoter and optionally animal protein and/or vegetable protein in purified water, a physiological saline solution or a buffer, the resulting solution is adjusted to a pH range of 3 to 7, preferably 4 to 6. The agent to be used for adjusting the pH value may be a conventional acid or base which is non-toxic and non-irritative to humans, for example, an organic acid (e.g. acetic acid, citric acid, etc.) and a weak base (e.g. sodium hydrogen carbonate, sodium acetate, etc.).

The suppositories of the present invention can be prepared by using a conventional suppository base such as Witepsol (trade mark), macrogol, glycerogelatin, and the like. Firstly, a liquid preparation containing biologically active polypeptide is mixed well with a suppository base by a mechanical mixing apparatus (e.g. Voltex Mixer, etc.) at a suitable temperature, that is, at the lowest temperature sufficient for obtaining suitable fluidity of the suppository base, and then the mixture is cooled in a suppository mold.

The film preparation of the present invention may be prepared by mixing well the above mentioned liquid preparation with a film base such as hydroxypropylmethyl cellulose, chitosan, pullulan, glucomannan, polyacrylate ester, and the like, followed by casting the mixture and then by evaporating or drying thereof.

The cream preparation of the present invention may be prepared in the form of either water-in-oil type or oil-in-water type which contains the composition of the present invention.

The tablets of the present invention may be prepared by mixing well a liquid preparation containing a biologically active polypeptide with an appropriate additive such as fillers, binding agents, disintegrators, and the like, followed by drying, and if necessary, by adding thereto other additives such as a lubricant, and the like, and then by tabletting the mixture with a tablet machine.

If necessary, a gas-releasing agent such as carbonates (e.g. $NaHCO_3$, etc.) or acid salts (e.g. tartrate, citrate, etc.) may be used as an additive to prepare an effervescent preparation.

When the tablets of the present invention are non-disintegrable, it is necessary to use a base which can form a hydrogel in the vagina. The base suitable for the above mentioned hydrogel is, for example, glucomannan, alginic acid and a calcium salt thereof, pectin, hydroxypropylmethyl cellulose, and the like. The disintegrable tablets show rapid-release properties, but the non-disintegrable tablets usually show slow-release properties.

The soft capsule preparation of the present invention may be prepared by encapsulating an oily preparation or polyethylene glycol preparation containing a biologically active polypeptide into soft capsules.

The tampon-shape preparation of the present invention may be prepared by various processes. The typical process comprises, for example, coating a tampon-shape core made of silicone resin with a polymer film containing a biologically active peptide, such as chitosan, polyacrylatemethacrylate copolymer, and the like.

In order to improve the quality and the appearance of the transvaginal preparation of the present invention, it may be incorporated with one or more additives, such as excipients, colorants, isotonic agents or antioxidants, for example, excipients such as starch, dextrin, mannitol, cyclodextrin, tragacanth, and the like; colorants such as $\beta$-carotin, red color No. 2, blue color No.1, and the like; isotonic agents such as sodium chloride, glucose, and the like; and antioxidants such as ascorbic acid, erythorbic acid or a salt or ester thereof [cf. Remington's Pharmaceutical Sciences, 17th, 1985, edited by Alfonso R. Gennaro, Mack Publishing Company, Easton, Pa. 18042].

By administering the transvaginal preparation of the present invention, the biologically active polypeptide therein is easily and effectively absorbed through the vaginal mucous membrane and shows the characteristic biological activity thereof. Moreover, the biologically active polypeptides, especially insulin and calcitonin are stable in the transvaginal preparation of the present invention, and the activity thereof does not change after the storage for a long period of time. If necessary, the transvaginal preparation of the present invention may be kept in a cold place in order to keep the stability thereof. Further, the transvaginal preparation of the present invention is less irritative to the vaginal mucous membrane.

The present invention is illustrated in more detail by the following Experiments and Preparations, but should not be construed to be limited thereto.

Experiment 1 The promotion effect of a combination of polyoxyethylenealkylphenyl ether and N-acylamino acid on absorption of elcatonin The ovaries of female Wistar rats (5–6 weeks old) were taken out, and the rats were fed for about one month, which was used as a model animal for postmenopausal woman in this Experiment. Age of the thus fed animals were between 17–21 weeks.

To elcatonin (400 ng) was added to bovine serum albumin (3 mg) and to the mixture was added as an absorption promoter a mixture of polyoxyethylenealkylphenyl ether (20 $\mu$l) and an N-acylamino acid (10 $\mu$g) in the ratios as shown in Table 1. The mixture was diluted with 0.1M acetic acid/sodium acetate buffer solution (pH 5.0) to give an elcatonin solution (1 ml).

The above rats were anesthetized with ether, and the required amount of the blood was collected therefrom through the right external jugular vein prior to administration of elcatonin.

After inserting a small cotton ball into the rat vagina, the above mentioned elcatonin solution (50 $\mu$l) was administered thereto. The blood thereof was collected again two hours after the administration of elcatonin.

The serum was separated from the whole blood, and the calcium level thereof was determined by using Calcium C Test Kit (trade mark) (Wako Pure Chemical Industries, Ltd.). The results are shown in Table 1.

TABLE 1

| Absorption promoter N-Acylamino acid (1.0%) | | Polyoxyethylenealkyl- phenyl ether* (2.0%) | Reduction rate of serum calcium level (%) |
|---|---|---|---|
| N-n-Hexanoylglycine sodium salt | + | NP-40 | 6.1 ± 1.5 |
| N-n-Octanoylglycine sodium salt | + | NP-40 | 5.3 ± 1.6 |
| N-n-Decanolyglycine sodium salt | + | NP-40 | 5.0 ± 1.6 |
| N-n-Dodecanolyglycine sodium salt | + | NP-40 | 4.3 ± 0.6 |

TABLE 1-continued

| Absorption promoter N-Acylamino acid (1.0%) | Polyoxyethylenealkyl-phenyl ether* (2.0%) | Reduction rate of serum calcium level (%) |
|---|---|---|
| N-n-Decanoylglutamic acid sodium salt | + NP-40 | 8.0 ± 2.9 |
| N-n-Decanoylphenylalanine sodium salt | + NP-40 | 6.7 ± 2.1 |
| N-n-Decanoylaspartic acid sodium salt | + NP-40 | 7.3 ± 1.7 |
| N-n-Decanoylaspartic acid sodium salt | + NP-15 | 6.0 ± 2.0 |
| N-n-Decanoylaspartic acid sodium salt | + NP-10 | 5.6 ± 2.2 |

*NP-40: Polyoxyethylene(9)octylphenyl ether
NP-15: Polyoxyethylene(15)nonylphenyl ether
NP-10: Polyoxyethylene(10)nonylphenyl ether Using as an absorption promoter polyoxyethylenealkylphenyl ether, N-acylamino acids, or other components alone, the control preparations for reference were prepared, and administered to the above mentioned rats in the same manner as above, and then, the decrease in serum calcium level was determined likewise. The results are shown in Table 2.

TABLE 2

| Absorption promoter | Reduction rate of serum calcium level (%) |
|---|---|
| 1.0% N-n-Decanoylglycine sodium salt | 2.3 ± 2.4 |
| 1.0% Deoxycholic acid sodium salt | 2.3 ± 1.2 |
| 1.0% aspartame | 0.3 ± 1.5 |
| 2.0% NP-40 | 0 ± 2.6 |

As is clear from above Tables 1 and 2, when a combination of polyoxyethylenealkylphenyl ether and N-acylamino acid is used as an absorption promoter, the preparation shows much higher reduction rate of serum calcium level than the preparation wherein they are used alone, and the absorption promoter composed of the above combination can extremely promote the absorption of elcatonin.

Experiment 2

In the same manner as described in Experiment 1 except using as an absorption promoter various combinations of N-n-decanoylglycine sodium salt and NP-40 in the various ratios as shown in Table 3, the reduction rate of serum calcium level was examined. The results are shown in Table 3.

TABLE 3

| Absorption promoter | | Reduction rate of serum calcium level (%) |
|---|---|---|
| N-n-Decanoylglycine sodium salt (%) | NP-40 (%) | |
| 0.01 | 2.0 | 2.8 ± 2.3 |
| 0.05 | 2.0 | 7.0 ± 2.3 |
| 0.1 | 2.0 | 8.0 |
| 0.5 | 2.0 | 4.8 ± 1.4 |
| 1.0 | 2.0 | 3.6 |
| 1.0 | 1.0 | 6.7 |
| 1.0 | 0.5 | 6.1 ± 1.6 |

Experiment 3 Promotion effect of absorption promoters comprising other combinations on absorption of elcatonin In the same manner as described in Experiment 1 except using as an absorption promoter a component (A) selected from cholic acids, pectic acid, taurine, saccharin sodium, glycyrrhizic acid and aspartame instead of the N-acylamino acid, and NP-40 [polyoxyethylene(9)octylphenyl ether] as polyoxyethylenealkylphenyl ether (B), the promotion effect thereof on the absorption of elcatonin was examined. The results are shown in Table 4.

TABLE 4

| Absorption promoter | | | Reduction Rate of serum calcium level (%) |
|---|---|---|---|
| (A) 1.0% | | (B) 2.0% | |
| Taurocholic acid sodium salt | + | NP-40 | 7.0 ± 2.4 |
| Deoxycholic acid sodium salt | + | NP-40 | 5.3 ± 2.0 |
| Chenodeoxycholic acid sodium salt | + | NP-40 | 4.6 ± 1.0 |
| Pectic acid | + | NP-40 | 6.9 ± 0.8 |
| Taurine | + | NP-40 | 6.7 ± 1.1 |
| Saccharin sodium | + | NP-40 | 6.7 ± 2.6 |
| Glycyrrhizic acid | + | NP-40 | 8.8 |
| Aspartame | + | NP-40 | 8.2 ± 1.8 |

As is clear from above Table 4 in comparison with Table 2, the preparation using the absorption promoter comprising the combination of the present invention showed quite higher reduction rate of serum calcium level than that of preparations using each of components alone.

Preparation 1

In the following formulation, transvaginal suppositories are prepared in a conventional manner.

| Components | Amount |
|---|---|
| Elcatonin | 40 μg |
| NP-40 | 200 mg |
| N-n-Hexanoylglycine sodium salt | 100 mg |
| Bovine serum albumin | 30 mg |
| 0.1 M Acetic acid/ sodium acetate buffer (pH 5) | 0.5 ml |
| Witepsol | q.s. |
| | Totally 10 g (for 5 pieces) |

Preparation 2

In the following formulation, transvaginal suppositories are prepared in a conventional manner.

| Component | Amount |
|---|---|
| Insulin | 1000 I.U. |
| NP-40 | 200 mg |
| N-n-Octanoylglycine sodium salt | 100 mg |
| Bovine serum albumin | 30 mg |
| 0.1 M Acetic acid/ sodium acetate buffer (pH 5) | 0.5 ml |
| Macrogol | q.s. |
| | Totally 10 g |

Preparation 3

In the following formulation, transvaginal suppositories are prepared in a conventional manner.

| Component | Amount |
| --- | --- |
| h-PTH (1–34) | 200 μg |
| NP-40 | 200 mg |
| N-n-Decanoylglycine sodium salt | 100 mg |
| Bovine serum albumin | 30 mg |
| 0.1 M Acetic acid/ sodium acetate buffer (pH 5) | 0.5 ml |
| Glycerogelatin | q.s. |
| | Totally 10 g (for 10 pieces) |

Preparation 4

In the following formulation, transvaginal suppositories are prepared in a conventional manner.

| Component | Amount |
| --- | --- |
| Porcine calcitonin | 600 I.U. |
| NP-40 | 200 mg |
| Taurocholic acid sodium salt | 100 mg |
| Bovine serum albumin | 30 mg |
| 0.1 M Acetic acid/ sodium acetate buffer (pH 5) | 0.5 ml |
| Witepsol | q.s. |
| | Totally 10 g (for 5 pieces) |

Preparation 5

In the following formulation, transvaginal suppositories are prepared in a conventional manner.

| Component | Amount |
| --- | --- |
| Salmon calcitonin | 50 μg |
| NP-40 | 200 mg |
| Taurocholic acid sodium salt | 100 mg |
| Bovine serum albumin | 30 mg |
| 0.1 M Acetic acid/ sodium acetate buffer (pH 5) | 0.5 ml |
| Witepsol | q.s. |
| | Totally 10 g (for 5 pieces) |

Preparation 6

In the following formulation, transvaginal suppositories are prepared in a conventional manner.

| Component | Amount |
| --- | --- |
| Salmon calcitonin | 50 μg |
| NP-40 | 200 mg |
| Pectic acid | 100 mg |
| Bovine serum albumin | 30 mg |
| 0.1 M Acetic acid/ sodium acetate buffer (pH 5) | 0.5 ml |
| Macrogol | q.s. |
| | Totally 10 g (for 5 pieces) |

Preparation 7

In the following formulation, transvaginal suppositories are prepared in a conventional manner.

| Component | Amount |
| --- | --- |
| Porcine calcitonin | 600 I.U. |
| NP-15* | 200 mg |
| N-n-Decanoylaspartic acid sodium salt | 100 mg |
| Bovine serum albumin | 30 mg |
| 0.1 M Acetic acid/ sodium acetate buffer (pH 5) | 0.5 ml |
| 15% PVA | q.s. |
| | Totally 10 g (for 5 pieces) |

*Polyoxyethylene(15)nonylphenyl ether

In the following formulation, transvaginal tablet is prepared in a conventional manner.

| Component | Amount |
| --- | --- |
| Elcatonin | 8 μg |
| NP-40 | 20 mg |
| N-n-Hexanoylglycine sodium salt | 10 mg |
| Bovine serum albumin | 3 mg |
| Carboxymethyl cellulose Na (CMC.Na) | 20 mg |
| Cornstarch | 300 mg |
| Lactose | q.s. |
| | Totally 1 g |

Preparation 9

In the following formulation, transvaginal tablet is prepared in a conventional manner.

| Component | Amount |
| --- | --- |
| Elcatonin | 6 μg |
| NP-40 | 20 mg |
| N-n-Hexanoylglycine sodium salt | 10 mg |
| Bovine serum albumin | 3 mg |
| CMC.Na | 20 mg |
| Cornstarch | 200 mg |
| Citric acid | 100 mg |
| Sodium hydrogen carbonate | 100 mg |
| Magnesium stearate | 50 mg |
| Lactose | q.s. |
| | Totally 1 g |

Preparation 10

In the following formulation, transvaginal cream is prepared in a conventional manner.

| Component | Amount |
| --- | --- |
| Elcatonin | 50 μg |
| NP-40 | 200 mg |
| N-n-Octanoylglycine sodium salt | 100 mg |
| Bovine serum albumin | 30 mg |
| White petrolatum | 2.5 g |
| Stearyl alcohol | 2.0 g |
| Propylene glycol | 1.0 g |

-continued

| Component | Amount |
| --- | --- |
| Monostearic acid glycerin | 0.5 g |
| Methylparaben | 10 mg |
| Purified water | q.s. |
| | Totally 10 g |

What is claimed is:

1. A high-absorbable transvaginal preparation comprising a calcitonin or a derivative thereof selected from the group consisting of salmon calcitonin, human calcitonin, porcine calcitonin, eel calcitonin and chicken calcitonin and an absorption promoter comprising a polyoxyethylenealkylphenyl ether, and one or more compounds selected from the group consisting of an amino acid N-acylated with an aliphatic carboxylic acid having 6 to 14 carbon atoms, cholic acids, pectic acid, taurine, saccharin, glycyrrhizic acid, aspartame, or a salt thereof.

2. The high-absorbable transvaginal preparation according to claim 1, wherein the derivative of eel calcitonin is (Asu1,7)-eel calcitonin (elcatonin).

3. The high-absorbable transvaginal preparation according to claim 1, wherein the polyoxyethylenealkylphenyl ether is polyoxyethylene(5-30)alkylphenyl ether.

4. The high-absorbable transvaginal preparation according to claim 5, wherein the polyoxyethylenealkylphenyl ether is polyoxyethylene(9)octylphenyl ether.

5. The high-absorbable transvaginal preparation according to claim 3, the polyoxyethylenealkylphenyl ether is selected from the group consisting of polyoxyethylene(10)octylphenyl ether, polyoxyethylene(30)octylphenyl ether, polyoxyethylene(10)nonylphenyl ether, polyoxyethylene(15)nonylphenyl ether and polyoxyethylene(20)nonylphenyl ether.

6. The high-absorbable transvaginal preparation according to claim 1, wherein the absorption promoter comprises a polyoxyethylenealkylphenyl ether and an amino acid N-acylated with an aliphatic carboxylic acid having 6-14 carbon atoms or a salt thereof.

7. The high-absorbable transvaginal preparation according to claim 6, wherein the N-acylated amino acid or a salt thereof is selected from the group consisting of N-n-hexanoylglycine, N-n-oxtanoylglycine, N-n-decanoylglycine, N-n-dodecanoylglycine, N-n-decanoylglutamic acid, N-n-decanoylphenylalanine, N-n-decanoylaspartic acid and a metallic salt thereof.

8. The high-absorbable transvaginal preparation according to claim 1, wherein the absorption promoter is incorporated in an amount of about 0.1 to 20% by weight of polyoxyethylenealkylphenyl ether, and about 0.01 to 5% by weight of one or more compounds selected from the group consisting of an amino acid N-acylated with an aliphatic carboxylic acid having 6-14 carbon atoms, cholic acids, pectic acid, taurine, saccharin, glycyrrhizic acid, aspartame and a salt thereof, based on the whole weight of the preparation.

9. The high-absorbable preparation according to claim 1, which is in a pharmaceutical dosage form selected from a liquid preparation, a gel preparation having a high viscosity, a suppository, a film preparation, a tablet, a tampon-shape preparation, and a cream preparation.

10. A highly absorbable transvaginal preparation which comprises elcatonin and an absorption promoter which comprises a polyoxyethylenealkylphenyl ether and an amino acid N-acylated with an aliphatic carboxylic acid having 6-14 carbon atoms.

11. A highly absorbable transvaginal preparation which comprises elcatonin and an absorption promoter which comprises polyoxyethylene-(9)octylphenyl ether and N-n-decanoyl-glycine.

* * * * *